United States Patent
Wong et al.

(10) Patent No.: US 11,208,631 B1
(45) Date of Patent: Dec. 28, 2021

(54) DUAL-ENZYME COMPOSITION FOR PREVENTING, TREATING AND/OR ALLEVIATING VEISALGIA AND SYMPTOMS ASSOCIATED THEREWITH

(71) Applicant: ALCOLEAR LIMITED, Hong Kong (HK)

(72) Inventors: Bing Lou Wong, Irvine, CA (US); Sek Lun Law, Hong Kong (HK)

(73) Assignee: ALCOLEAR LIMITED, Hong Kong (HK)

( * ) Notice: Subject to any disclaimer, the term of this patent is extended or adjusted under 35 U.S.C. 154(b) by 0 days.

(21) Appl. No.: 17/308,995

(22) Filed: May 5, 2021

(51) Int. Cl.
| | |
|---|---|
| *C12N 9/02* | (2006.01) |
| *A61P 3/00* | (2006.01) |
| *A61P 25/32* | (2006.01) |
| *C12N 9/04* | (2006.01) |

(52) U.S. Cl.
CPC .............. *C12N 9/0008* (2013.01); *A61P 3/00* (2018.01); *A61P 25/32* (2018.01); *C12N 9/0006* (2013.01); *C12Y 101/01001* (2013.01); *C12Y 102/01003* (2013.01)

(58) Field of Classification Search
None
See application file for complete search history.

(56) References Cited

U.S. PATENT DOCUMENTS

| | | | |
|---|---|---|---|
| 5,759,539 | A | 6/1998 | Whitmire |
| 10,245,288 | B2 | 4/2019 | Kovarik |
| 2005/0271739 | A1 | 12/2005 | Wang |
| 2020/0330546 | A1 | 10/2020 | Chung et al. |

FOREIGN PATENT DOCUMENTS

| | | |
|---|---|---|
| CN | 103911335 B | 4/2016 |

OTHER PUBLICATIONS

Substance Abuse and Mental Health Services Administration. "Key substance use and mental health indicators in the United States: Results from the 2018 National Survey on Drug Use and Health" Center for Behavioral Health Statistics and Quality, Substance Abuse and Mental Health Services Administration. 2019.
Jeffrey J. Sacks et al. "2010 National and State Costs of Excessive Alcohol Consumption." American Journal of Preventive Medicine, 2015 (49:5), p. e73-e79.
Hui G. Cheng et al. "Prevalence of alcohol use disorders in mainland China: a systematic review." Addiction, 2015 (110), p. 761-774.
Lena L. Lim et al. "Role of collective self-esteem on youth violence in a collective culture." International Journal of Psychology, 2009 (44:1), p. 71-78.
Chencheng Xie et al. "Role of Probiotics in Non-alcoholic Fatty Liver Disease: Does Gut Microbiota Matter?" Nutrients, 2019 (11:2837), p. 1-22.
Aishwarya Nene et al. "Aldehyde dehydrogenase 2 activation and coevolution of its εPKC-mediated phosphorylation sites" Journal of Biomedical Science, 2017 (24:3), p. 1-12.
Thomas D. Hurley et al. "Pharmacogenomics of Alcoholism." In Pharmacogenomics: The Search for Individualized Therapies, Weinheim: Wiley-VCH, 2002, p. 417-441.

*Primary Examiner* — Kagnew H Gebreyesus
(74) *Attorney, Agent, or Firm* — Idea Intellectual Limited; Margaret A. Burke; Sam T. Yip

(57) ABSTRACT

A composition including two exogenous enzymes from animals for consumption by human being before and/or after consuming alcohol to prevent, treat and/or alleviate veisalgia and/or symptoms associated therewith arising from or caused by excessive consumption of alcohol through a dual-enzyme based breakdown of the excess alcohol is provided, wherein a first enzyme of the two exogenous enzymes is capable of converting alcohol into a first metabolite while a second enzyme thereof is capable of converting the first metabolite into a second metabolite which is excretable to systemic circulation after an oxidation reaction of the alcohol in the presence of the two exogenous enzymes and $NAD^+/NADH$; the first enzyme to the second enzyme is in a molar ratio that maintains a ratio between the first and second metabolites in the human being so as to avoid local elevation of the first metabolite in the human being after consumption of excess alcohol.

7 Claims, 4 Drawing Sheets
Specification includes a Sequence Listing.

DUAL-ENZYME COMPOSITION FOR PREVENTING, TREATING AND/OR ALLEVIATING VEISALGIA AND SYMPTOMS ASSOCIATED THEREWITH

FIELD OF THE INVENTION

The present invention relates to a dual-enzyme composition for preventing, treating and/or alleviating veisalgia and symptoms associated therewith, and, more particularly, to assisted enzyme-based breakdown of alcohol within the human body.

BACKGROUND

Alcoholism or Alcohol Use Disorder ("AUD") is a chronic relapsing brain disease characterized by an impaired ability to stop or control alcohol use despite adverse social, occupational, and health consequences. AUD puts people at risk for many adverse health consequences, including Alcoholic Liver Disease, acute alcohol intoxication and various cancers. According to the global status report on alcohol and health report by WHO for 2018, the harmful use of alcohol resulted in some 3 million deaths (5.3% of all deaths) worldwide in the year 2016. Mortality resulting from alcohol consumption is higher than that caused by diseases such as tuberculosis, HIV/AIDS and diabetes.

The effect of ingested beverage alcohol (ethanol) on different organs in human body, including the brain/Central Nervous System, liver & pancreas, depends on the ethanol concentration intake and the duration of exposure. Both of these variables are affected by the absorption of ethanol into the blood stream and tissues as well as by ethanol metabolism[5]. The primary enzymes in the human body involved in ethanol metabolism are Alcohol Dehydrogenase ("ADH") and Aldehyde Dehydrogenase ("ALDH"). The main pathway of ethanol metabolism involves its oxidation to acetaldehyde, a reaction that is catalysed by ADH and co-enzyme NAD+. In a second reaction catalyzed by ALDH and co-enzyme NAD+, acetaldehyde is oxidized to acetic acid. It is illustrated as FIG. 1. The mechanism through which ADH and ALDH influences alcoholism risk is thought to involve local elevation of acetaldehyde levels, resulting either from a more rapid ethanol oxidation or from a slower acetaldehyde oxidation. Acetaldehyde is a toxic substance, whose accumulation leads to highly adverse reactions that include facial flushing, nausea, rapid heart rate and veisalgia, and symptoms associated therewith (FIG. 1).

Recently, many people use over-the-counter pain relievers, like aspirin or acetaminophen, to relieve veisalgia and symptoms associated therewith. It is important to recognize that the combination of alcohol and acetaminophen can be toxic to the liver. Furthermore, there is no medication for acute alcohol intoxication. Haemodialysis is the only option in emergency cases, especially in the US, where the medicine Metadoxin has not been approved by the FDA. Consequently, the development of innovative preventive measures which can effectively minimize the risk of potential health hazards brought about by drinking alcohol has become a very important strategy to lessen the burden on the overall economy. There is a huge void in the healthcare market for a product which is effective, safe and convenient for daily use as a prophylaxis measure for casual and frequent alcohol drinkers and AUD patients.

As seen from the various alcohol ingestion-related, there is a need in the art to enhance the breakdown of alcohol in the human body. Enhanced breakdown of alcohol and alcohol metabolism products would reduce long-term harmful effects from alcohol such as liver damage, and short-term effects such as veisalgia and alcohol poisoning. Thus, there is a need in the art for compositions that can enhance the breakdown of alcohol in the human body that are low-cost and have minimal side effects.

SUMMARY OF THE INVENTION

In one aspect, there is provided a composition including two exogenous enzymes from animals for consumption by human being before and/or after consuming alcohol to prevent, treat and/or alleviate veisalgia and/or symptoms associated therewith arising from or caused by excessive consumption of alcohol through a dual-enzyme based breakdown of the excess alcohol, wherein a first enzyme of the two exogenous enzymes is capable of converting alcohol into a first metabolite while a second enzyme thereof is capable of converting the first metabolite into a second metabolite which is excretable to systemic circulation after an oxidation reaction of the alcohol in the presence of the two exogenous enzymes and NAD+/NADH, and wherein the first enzyme to the second enzyme is in a molar ratio of 1:15-60 in the composition in order to maintain a ratio between the first and second metabolites in the human being so as to avoid local elevation of the first metabolite in the human being after consumption of excess alcohol.

In one embodiment, the first enzyme is alcohol dehydrogenase and the second enzyme is aldehyde dehydrogenase.

In another embodiment, the first enzyme to the second enzyme in the composition is in a molar ratio of 1:40.

In other embodiment, the local elevation of the first metabolite leads to veisalgia symptoms.

In yet another embodiment, the first metabolite is acetaldehyde.

In other embodiment, the second metabolite is acetate.

In also another embodiment, the symptoms associated with veisalgia comprise fatigue, apathy, concentration problems, clumsiness, confusion, thirst, sweating, shivering, stomach pain, nausea, dizziness and heart pounding.

In an embodiment, the aldehyde dehydrogenase is represented by an amino acid sequence of SEQ ID NO: 1.

In an embodiment, the animals from which the two exogenous enzymes are comprise bovine and ovine.

In other embodiment, the exogenous enzymes are from livers of bovine and ovine.

DEFINITIONS

The following abbreviations and their corresponding long expressions are used herein interchangeably:

| ADH | — | Alcohol Dehydrogenase |
| AHSS | — | Alcohol Hangover Severity Scale |
| ALDH | — | Aldehyde Dehydrogenase |
| AUD | — | Alcohol Use Disorder |
| FDA | — | Food and Drug Administration |
| I.M. | — | intramuscular |
| I.V. | — | intravenous |
| US | — | United States |
| WHO | — | World Health Organization |

DETAILED DESCRIPTION

1. Mechanism of the Present Invention:

Enzymes are macromolecular biological catalysts, which can accelerate chemical reactions in the human body. Almost all metabolic processes in cells need enzyme catalysis in order to occur at rates fast enough to sustain life. Enzymes are known to catalyse more than 5,000 biochemical reactions. Most enzymes are proteins, and the specificity comes from their unique three-dimensional structures. As many enzymes are naturally produced by the human body, they are safe use as supplements that may be ingested.

The present invention focuses on two enzymes for alcohol metabolism, namely Alcohol Dehydrogenase ("ADH") and Aldehyde Dehydrogenase ("ALDH"). ADH is an enzyme found primarily in the liver and stomach that converts ethanol to acetaldehyde, a toxin which is then further broken down by ALDH to acetic acid, which can be converted to carbon dioxide and water. These two enzymes were studied using in vitro assays, proving that the corresponding enzymatic activity is highly potent, and could potentially be used to enhance the degradation of alcohol in the human body for frequent alcohol drinkers to prevent from as well as treat and/or alleviate veisalgia and symptoms associated therewith. These enzymes may also be used to treat those whose faulty microbiomes are overproducing ethanol from non-alcohol-based food and beverages.

In one aspect, ADH and ALDH were tested, in vitro, to determine activity on ethanol substrates. The ADH and ALDH were sourced from mammal livers, a plentiful natural source for the starting material that can contribute to production of a low-cost oral supplement.

Figure 1:
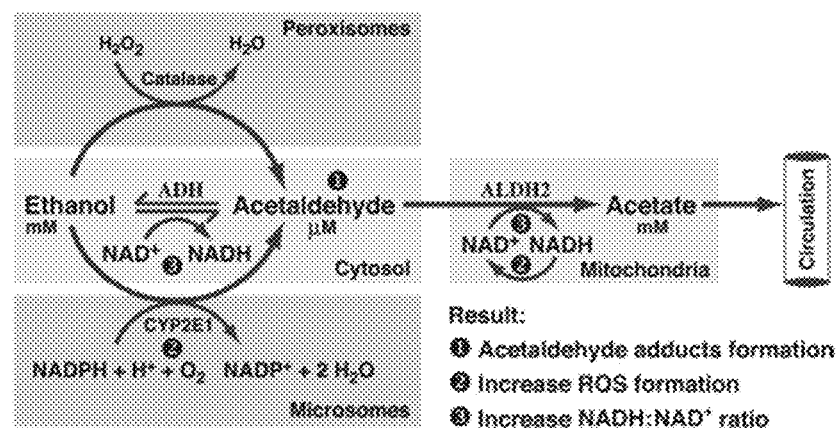
FIG. 1 schematically illustrates the general mechanism of how ADH and ALDH2 metabolize alcohol in a human body.
Figure 2:
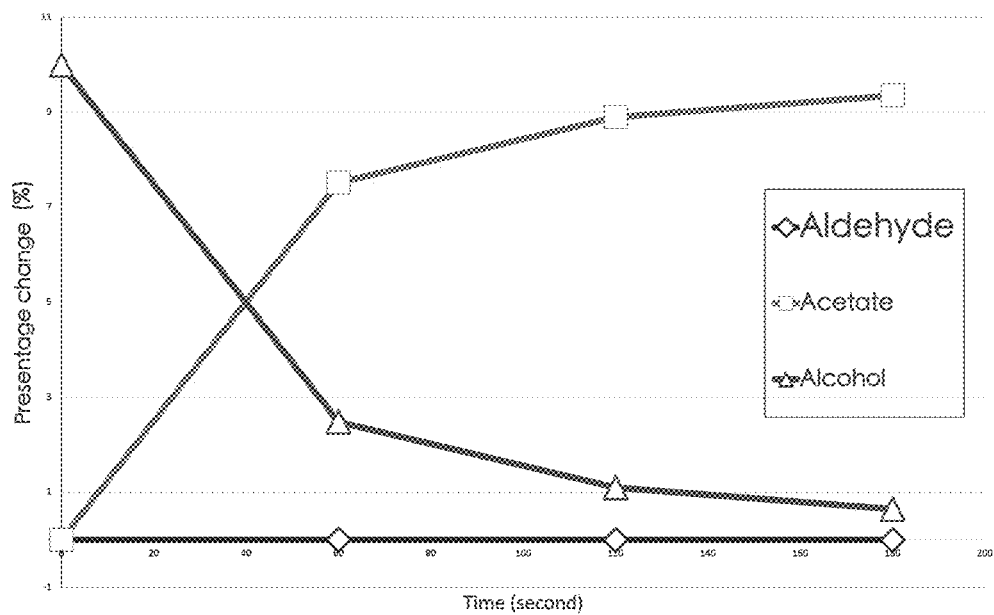
FIG. 2 shows the result of in vitro enzymatic activity of the present composition in term of the change in concentration of alcohol and its by-products or metabolites over time.

The bovine or ovine liver is sourced from Australia. The enzymes tested use an ideal ratio of ADH and ALDH ranging from 1:15-60, and more preferably is 1:40, to enable the second step of the enzymatic alcohol degradation process to be the dominant enzymatic reaction. The rationale for developing such a formulation is to prevent the accumulation of acetaldehyde, which is the major cause of veisalgia and symptoms associated therewith. Using this formulation, acetaldehyde, the breakdown product from alcohol in the first step of enzymatic process, is effectively degraded to acetic acid and eventually water and carbon dioxide. The in vitro enzymatic activity of this special formulation is illustrated in FIG. 2.

2. Formulations Used in the Present Invention

In one aspect, the present invention produces a high-quality therapeutic enzyme remedy in an enteric capsule form to enhance degradation of alcohol in the human body, in order to relieve veisalgia and symptoms associated therewith for both casual and frequent alcohol drinkers. It is a freeze-dried powder extracted from bovine or ovine liver by proprietary extraction and isolation methods that produce a product safe for human consumption and effective for alcohol degradation.

Using proprietary extraction and isolation methods, ADH and ALDH enzymes are successfully extracted from livers of different origin, including cows and sheep. The extracts were freeze-dried and stored as dried powder. The extract/freeze-dried powder from different animal origins were very consistent with the ADH and ALDH enzymes contents in the ideal molar ratio of ADH and ALDH. The in vitro enzymatic activity results from livers of cow and sheep (when concentration of liver extract is about 50 mg/ml) for ADH is on average 0.843 Unit and 0.808 Unit, respectively, and for ALDH is on average 30.453 Unit and 29.322 Unit, respectively.

From the in-house stability test of the freeze-dried powder, it shows very good stability when stored more than 12 months at room temperature and dry humidity.

Figure 3:
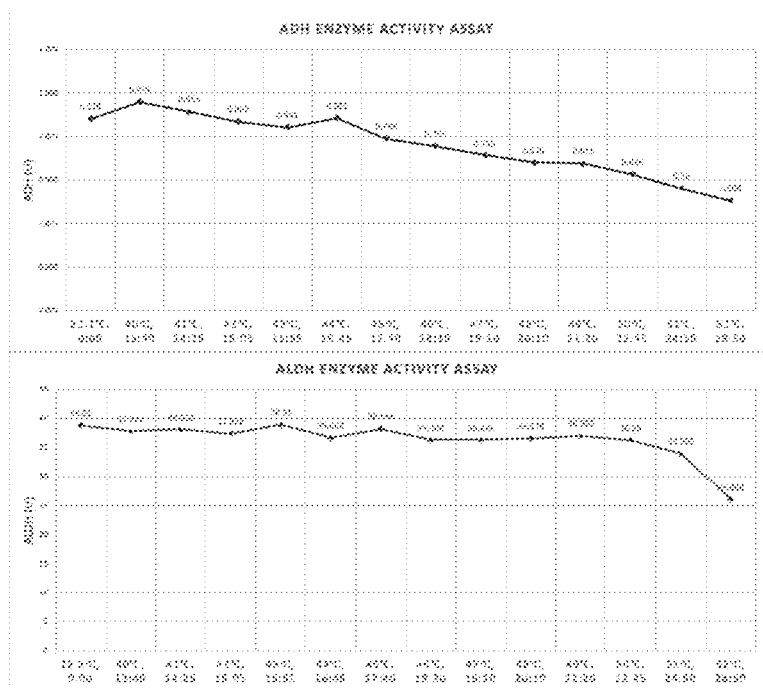
FIG. 3 shows the result of in vitro enzymatic activity of the contents of ADH & ALDH in the heat up process of the extract.

The present invention uses proprietary extraction method. Proprietary extraction means precisely control the heat up and cool down processes of the extract from mammalian livers. It is found that when extract from liver was heated up to 40° C., an extract with the highest content of ADH, together with ADH & ALDH enzymes contents roughly in the ideal molar ration of 1:40, could be obtained. The in vitro enzymatic activity of contents of ADH & ALDH in this heat up process is illustrated in FIG. 3.

The therapeutic enzyme of the present invention could not be produced from swine liver. From an in vitro study of the present invention, ALDH was not present in the extract from swine liver, where ALDH is one of the main components in the present composition.

Optionally, the extracted enzymes may be packaged with antioxidants in enteric capsules. Antioxidants, along with other optional excipients, can protect the enzymes from degradation in order to maintain a longer shelf-life with maximum efficacy.

Oral supplements according to the present invention may be used in the following: 1. Enhance alcohol metabolism in the human body in order to relieve veisalgia and symptoms associated therewith.

2. Degrade alcohol to prevent Alcoholic Liver Disease ("ALD").

Figure 4:
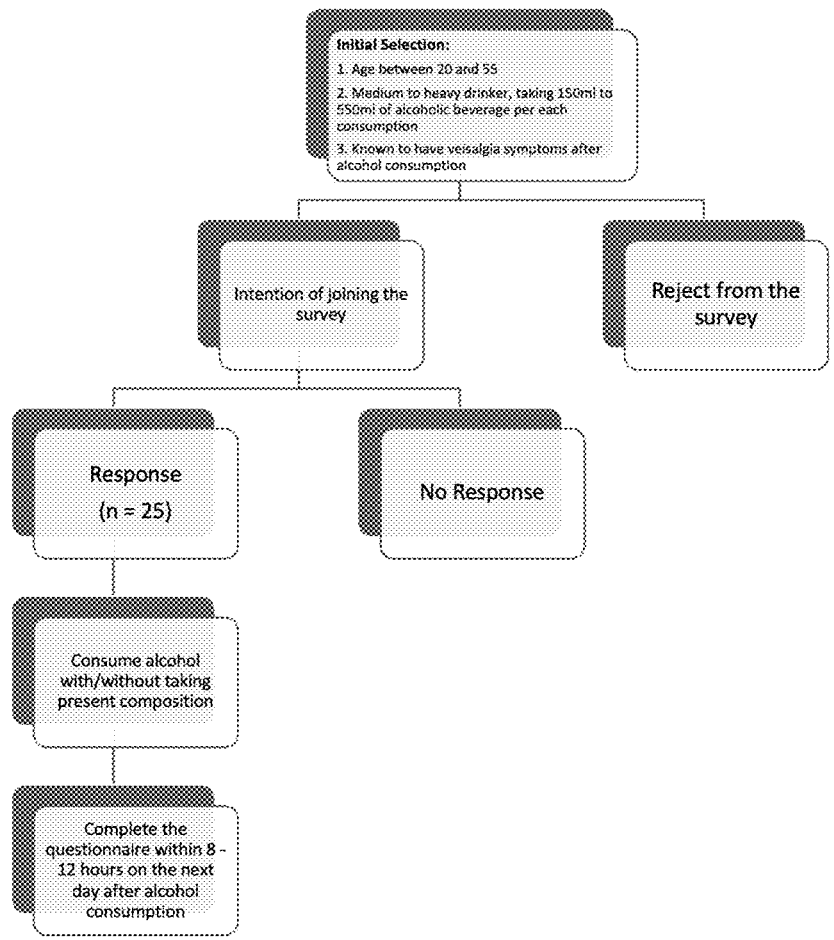
FIG. 4 shows the basic criteria of a survey to the effect of the present composition of this invention on the severity of veisalgia by using Alcohol Hangover Severity Scale (AHSS).

A survey was conducted by selecting subjects fulfilling the basic criteria shown in FIG. 4 to evaluate the effect of the present composition of this invention on the severity of veisalgia by using Alcohol Hangover Severity Scale (AHSS).

Twenty-five subjects were successfully recruited and were asked to complete same questionnaire twice during the 1 month test period. The subjects was drank 150 ml to 550 ml of alcoholic beverage in the dinner with alcohol content ranging from 15% to 55%. The questionnaire was completed 8-12 hours on the next day after alcohol consumption, where one questionnaire for each subject was completed under their normal alcohol intake practice, and the other was completed with taking the present composition of this invention before alcohol consumption. Twelve symptoms including fatigue, apathy, concentration problems, clumsiness, confusion, thirst, sweating, shivering, stomach pain, nausea, dizziness and heart pounding were used to evaluate the severity of veisalgia for all subjects The subjects were asked to indicate to what extent they experience the 12 symptoms mentioned above when wake up. It can be seen that 2 subjects did not develop veisalgia and/or any symptoms associated therewith, no matter with or without taking the present composition during the test period; 22 subjects developed veisalgia and/or symptoms associated therewith, in the absence of the present composition, but veisalgia or the associated symptoms was/were relieved after taking the present composition; 1 subject developed veisalgia and the associated symptoms, whether or not the present composition was taken. From the AHSS survey, about 88% of the subjects have positive response towards to the present composition, with significant relieve of their veisalgia and the associated symptoms after the alcohol consumption.

At higher doses, the enzyme compositions of the present invention may be used as an oral or injectable medication which can rapidly remove alcohol in emergency situations of acute alcohol intoxication. The present composition can reduce and prevent the severity of acute alcohol intoxication by efficiently converting alcohol to non-harmful substances before body tissues and organs, for instance, liver, uptake harmful levels of alcohol from blood.

For injectable formulations and optionally for oral formulations, recombinant DNA technology by introducing mammalian expression vectors carrying genes of human h-ADH and h-ALDH into safe and well-studied mammalian cell lines may be employed. These mammalian-cells-expressed target enzymes are further isolated and purified by chromatographic techniques. The present invention is useful to produce clinical grade h-ADH and h-ALDH for effective intravenous ("I.V.") or intramuscular ("I.M.") infusion of therapeutic enzyme remedies for emergency use in hospitals and clinics.

The human genome includes 19 ALDH genes. ALDH1 is primarily found in the liver and may be used in the enzyme extract version of the present invention. Another ALDH is ALDH2 which is found in the mitochondria. ALDH2 may be selected as the ALDH used in the present invention; its sequence is represented by SEQ ID NO: 1:
MSAAATQAVP APNQQPEVFC NQIFINNEWH DAVSRKTFPT VNPSTGEVIC QVAEGDKEDV DKAVKAARAA FQLGSPWRRM DASHRGRLLN RLADLIERDR TYLAALETLD NGKPYVISYL VDLDMVLKCL RYYAGWADKY HGKTIPIDGD FFSYTRHEPV GVCGQIIPWN FPLLMQAWKL GPALATGNVV VMKVAEQTPL TALYVANLIK EAGFPPGWN IVPGFGPTAG AAIASHEDVD KVAFTGSTEI GRVIQVAAGS SNLKRVTLEL GGKSPNIIMS DADMDWAVEQ AHFALFFNQG QCCCAGSRTF VQEDIYDEFV ERSVARAKSR VVGNPFDSKT EQGPQVDETQ FKKILGYINT GKQEGAKLLC GGGIAADRGY FIQPTVFGDV QDGMTIAKEE IFGPVMQILK FKTIEEVVGR ANNSTYGLAA AVFTKDLDKA NYLSQALQAG TVWVNCYDVF GAQSPFGGYK MSGSGRELGE YGLQAYTEVK TVTVKVPQKN S Recombinant ALDH such as ALDH2 is commercially available from suppliers such as Sigma Aldrich. Examples of recombinant techniques to product ALD and ALDH are described in Nene et al., J. Biomed. Sci. 2017, 24: 3, published 5 Jan. 2017, the disclosure of which is incorporated by reference herein.

The active ingredients in the formulation of the present invention may be incorporated into an oral formulation that may be administered as a dietary supplement product. A potential health benefit of this product is to relieve veisalgia and the associated symptoms for casual and frequent alcohol drinkers. The product should be taken before consuming alcohol.

REFERENCES

The disclosures of each of the following references are incorporated by reference herein.
1. Thomas D. Hurley, Howard J. Edenberg, Ting-Kai Li. Pharmacogenomics of Alcoholism. In: Pharmacogenomics: The Search for Individualized Therapies, Germany Wiley-VCH, Weinheim, Chapter 21, p. 417-441.
2. Nene et al., J. Aldehyde dehydrogenase 2 activation and coevolution of its cPKC-mediated phosphorylation sites. Biomed. Sci. 2017, 24: 3.

---

What is claimed is:

1. A composition comprising two exogenous enzymes are derived from animals and orally administered to a human being before and/or after consuming alcohol to prevent, treat and/or alleviate veisalgia and/or symptoms associated therewith arising from or caused by excessive consumption of alcohol through a dual-enzyme based breakdown of the excess alcohol, wherein a first enzyme of the two exogenous enzymes is capable of converting alcohol into a first metabolite while a second enzyme thereof is capable of converting the first metabolite into a second metabolite which is excretable to systemic circulation after an oxidation reaction of the alcohol in the presence of the two exogenous enzymes and NAD*/NADH, and wherein the first enzyme to the second enzyme is in a molar ratio of 1:40 in the composition in order to maintain a ratio between the first and second metabolites in the human being so as to avoid local elevation of the first metabolite in the human being after consumption of excess alcohol, and wherein said first enzyme is alcohol dehydrogenase and said second enzyme is aldehyde dehydrogenase, and wherein the animals from which the two exogenous enzymes are bovine and ovine.

2. The composition of claim 1, wherein the local elevation of the first metabolite leads to veisalgia symptoms.

3. The composition of claim 1, wherein the first metabolite is acetaldehyde.

4. The composition of claim 1, wherein the second metabolite is acetate.

5. The composition of claim 1, wherein the symptoms associated with veisalgia comprise fatigue, apathy, concentration problems, clumsiness, confusion, thirst, sweating, shivering, stomach pain, nausea, dizziness and heart pounding.

6. The composition of claim 1, wherein the aldehyde dehydrogenase is represented by an amino acid sequence of SEQ ID NO: 1.

7. The composition of claim 1, wherein the exogenous enzymes are from livers of bovine and ovine.

* * * * *

SEQUENCE LISTING

```
<160> NUMBER OF SEQ ID NOS: 1

<210> SEQ ID NO 1
<211> LENGTH: 501
<212> TYPE: PRT
<213> ORGANISM: Homo sapiens

<400> SEQUENCE: 1

Met Ser Ala Ala Ala Thr Gln Ala Val Pro Ala Pro Asn Gln Gln Pro
1               5                   10                  15

Glu Val Phe Cys Asn Gln Ile Phe Ile Asn Asn Glu Trp His Asp Ala
            20                  25                  30

Val Ser Arg Lys Thr Phe Pro Thr Val Asn Pro Ser Thr Gly Glu Val
        35                  40                  45

Ile Cys Gln Val Ala Glu Gly Asp Lys Glu Asp Val Asp Lys Ala Val
    50                  55                  60

Lys Ala Ala Arg Ala Ala Phe Gln Leu Gly Ser Pro Trp Arg Arg Met
65                  70                  75                  80

Asp Ala Ser His Arg Gly Arg Leu Leu Asn Arg Leu Ala Asp Leu Ile
                85                  90                  95

Glu Arg Asp Arg Thr Tyr Leu Ala Ala Leu Glu Thr Leu Asp Asn Gly
            100                 105                 110

Lys Pro Tyr Val Ile Ser Tyr Leu Val Asp Leu Asp Met Val Leu Lys
```

```
                115              120              125
Cys Leu Arg Tyr Tyr Ala Gly Trp Ala Asp Lys Tyr His Gly Lys Thr
        130              135              140
Ile Pro Ile Asp Gly Asp Phe Phe Ser Tyr Thr Arg His Glu Pro Val
145              150              155              160
Gly Val Cys Gly Gln Ile Ile Pro Trp Asn Phe Pro Leu Leu Met Gln
                165              170              175
Ala Trp Lys Leu Gly Pro Ala Leu Ala Thr Gly Asn Val Val Val Met
        180              185              190
Lys Val Ala Glu Gln Thr Pro Leu Thr Ala Leu Tyr Val Ala Asn Leu
        195              200              205
Ile Lys Glu Ala Gly Phe Pro Pro Gly Val Val Asn Ile Val Pro Gly
        210              215              220
Phe Gly Pro Thr Ala Gly Ala Ala Ile Ala Ser His Glu Asp Val Asp
225              230              235              240
Lys Val Ala Phe Thr Gly Ser Thr Glu Ile Gly Arg Val Ile Gln Val
                245              250              255
Ala Ala Gly Ser Ser Asn Leu Lys Arg Val Thr Leu Glu Leu Gly Gly
                260              265              270
Lys Ser Pro Asn Ile Ile Met Ser Asp Ala Asp Met Asp Trp Ala Val
        275              280              285
Glu Gln Ala His Phe Ala Leu Phe Phe Asn Gln Gly Gln Cys Cys Cys
        290              295              300
Ala Gly Ser Arg Thr Phe Val Gln Glu Asp Ile Tyr Asp Glu Phe Val
305              310              315              320
Glu Arg Ser Val Ala Arg Ala Lys Ser Arg Val Val Gly Asn Pro Phe
                325              330              335
Asp Ser Lys Thr Glu Gln Gly Pro Gln Val Asp Glu Thr Gln Phe Lys
                340              345              350
Lys Ile Leu Gly Tyr Ile Asn Thr Gly Lys Gln Glu Gly Ala Lys Leu
                355              360              365
Leu Cys Gly Gly Gly Ile Ala Ala Asp Arg Gly Tyr Phe Ile Gln Pro
        370              375              380
Thr Val Phe Gly Asp Val Gln Asp Gly Met Thr Ile Ala Lys Glu Glu
385              390              395              400
Ile Phe Gly Pro Val Met Gln Ile Leu Lys Phe Lys Thr Ile Glu Glu
                405              410              415
Val Val Gly Arg Ala Asn Asn Ser Thr Tyr Gly Leu Ala Ala Ala Val
                420              425              430
Phe Thr Lys Asp Leu Asp Lys Ala Asn Tyr Leu Ser Gln Ala Leu Gln
        435              440              445
Ala Gly Thr Val Trp Val Asn Cys Tyr Asp Val Phe Gly Ala Gln Ser
        450              455              460
Pro Phe Gly Gly Tyr Lys Met Ser Gly Ser Gly Arg Glu Leu Gly Glu
465              470              475              480
Tyr Gly Leu Gln Ala Tyr Thr Glu Val Lys Thr Val Thr Val Lys Val
                485              490              495
Pro Gln Lys Asn Ser
            500
```